United States Patent [19]

Ogata et al.

[11] 4,041,026
[45] Aug. 9, 1977

[54] 1,5-DIHYDRO-2H-1,4-BENZODIAZEPIN-2-ONE DERIVATIVES

[75] Inventors: Masaru Ogata, Kobe; Hiroshi Matsumoto, Takatsuki, both of Japan

[73] Assignee: Shionogi & Co., Ltd., Osaka, Japan

[21] Appl. No.: 720,832

[22] Filed: Sept. 7, 1976

[30] Foreign Application Priority Data

Sept. 11, 1975 Japan .................................. 50-110753

[51] Int. Cl.$^2$ ........................................... C07D 243/24
[52] U.S. Cl. ............................... 260/239.3 D; 424/244
[58] Field of Search ................................ 260/239.3 D

[56] References Cited

U.S. PATENT DOCUMENTS 3,803,129    4/1974    McCaully et al. ........... 260/239.3 D Primary Examiner—Henry R. Jiles
Assistant Examiner—Robert T. Bond
Attorney, Agent, or Firm—Wenderoth, Lind & Ponack

[57] ABSTRACT 1,5-Dihydro-2H-1,4-benzodiazepin-2-one derivatives of the formula:

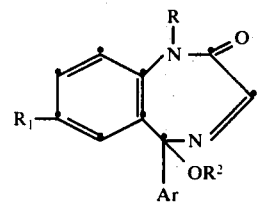

(wherein Ar represents pyridyl, phenyl, or halogenophenyl; R represents $C_1$–$C_6$ alkyl or $C_1$–$C_6$ alkyl substituted by a member selected from the group consisting of trifluoromethyl, cyano, carbamoyl, $C_2$–$C_{10}$ dialkylamino, and hydroxy; $R^1$ represents halogen, nitro, trifluoromethyl, or cyano; and $R^2$ represents $C_1$–$C_6$ alkyl or $C_1$–$C_6$ alkyl substituted by a member selected from the group consisting of halogen, hydroxy, and $C_1$–$C_6$ alkoxy), being useful as anxiolytics, sedatives, anticonvulsants, hypnotics, or their synthetic intermediates, are prepared.

5 Claims, No Drawings

1,5-DIHYDRO-2H-1,4-BENZODIAZEPIN-2-ONE DERIVATIVES

The present invention relates to 1,5-dihydro-2H-1,4-benzodiazepin-2-one derivatives of the formula:

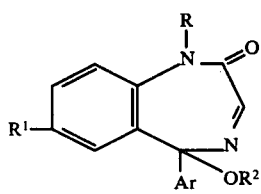

(wherein Ar represents pyridyl, phenyl, or halogenophenyl; R represents $C_1$-$C_6$ alkyl or $C_1$-$C_6$ alkyl substituted by a member selected from the group consisting of trifluoremethyl, cyano, carbamoyl, $C_2$-$C_{10}$ dialkylamino, and hydroxy; $R^1$ represents halogen, nitro, trifluoremethyl, or cyano; and $R^2$ represents $C_1$-$C_6$ alkyl or $C_1$-$C_6$ alkyl substituted by a member selected from the group consisting of halogen, hydroxy, and $C_1$-$C_6$ alkoxy), being useful as anxiolytics, sedatives, anticonvulsants, hypnotics, or their synthetic intermediates, and to the production thereof.

Illustrative explanation is given to the above definition as follows: alkyl (e.g. methyl, ethyl, propyl, isopropyl, butyl, isobutyl, pentyl, hexyl), alkoxy (e.g. methoxy, ethoxy, propoxy, butoxy, pentoxy), dialkylamino (e.g. dimethylamino, diethylamino, dipropylamino, dibutylamino, methylpropylamino), and halogen (e.g. chlorine, bromine, fluorine).

The 1,5-dihydro-2H-1,4-benzodiazepin-2-one derivatives (I) involve illustratively:

7-chloro-5-methoxy-1-methyl-5-phenyl-1,5-dihydro-2H-1,4-benzodiazepin-2-one; and
5-methoxy-1-methyl-7-nitro-5-phenyl-1,5-dihydro-2H-1,4-benzodiazepin-2-one.

The objective compounds (I) can be prepared through two routes (Routes A and B) as shown in the following scheme:

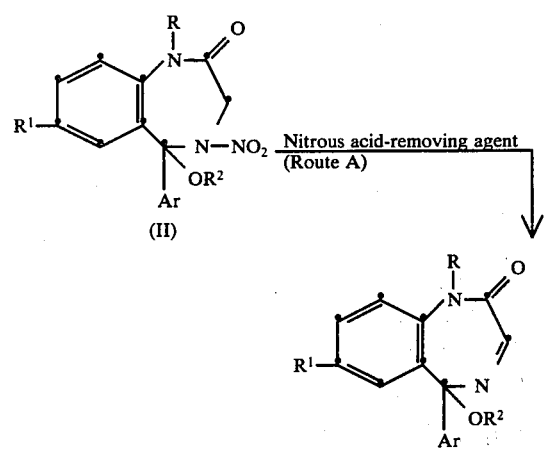

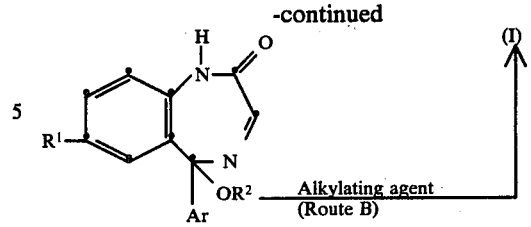

(wherein Ar, R, $R^1$, and $R^2$ each is as defined above).

Preferred embodiments of the above routes are illustratively explained in the following description.

Route A

This route is effected by reacting the starting compound (II) with a nitrous acid-removing agent such as alkali hydroxide (e.g. sodium hydroxide, potassium hydroxide), alkali alkoxide (e.g. sodium methoxide, potassium ethoxide), or tertary amine (e.g. triethylamine, pyridine, dimethylaniline) in a suitable solvent (e.g. dimethylformamide, hexamethylphosphoric triamide, dimethylsulfoxide, dioxane, methanol, ethanol, methylene chloride, dichloroethane, chloroform, their mixture) at room temperature or under cooling or heating.

The starting compound (II) can be prepared from the corresponding 1,3-dihydro-2H-benzodiazepin-2-one (IV) as shown in the following scheme:

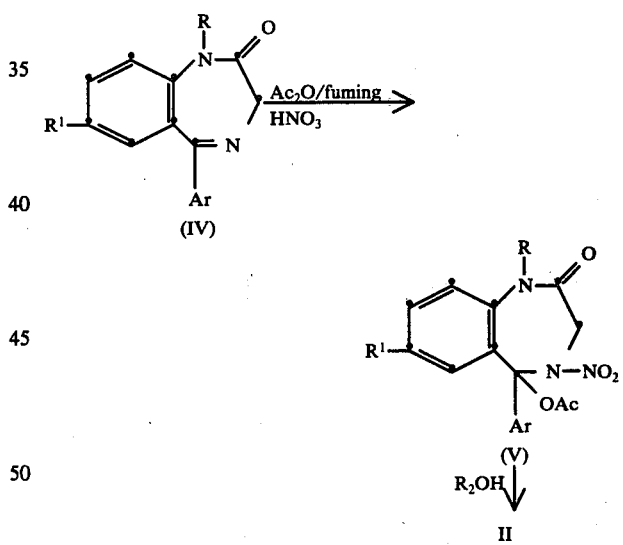

(wherein Ac represents acetyl; and Ar, R, $R^1$, and $R^2$ each is as defined above).

Route B

This route is effected by reacting the starting compound (III) with an alkylating agent containing the desired R moiety (e.g. methyl iodide, dimethyl sulfate, illustrating methylation) in the presence of a suitable base such as alkali hydroxide (e.g. sodium hydroxide, potassium hydroxide) or alkali alkoxide (e.g. sodium methoxide, potassium ethoxide). The reaction is carried out in an inert solvent (e.g. dimethylformamide, dimethylsulfoxide, hexamethylphosphoric triamide, methanol, ethanol) at room temperature or under cooling.

The starting compound (III) can be prepared from the corresponding 1,3-dihydro-2H-1,4-benzodiazepin-2-one (IVa) as shown in the following scheme:

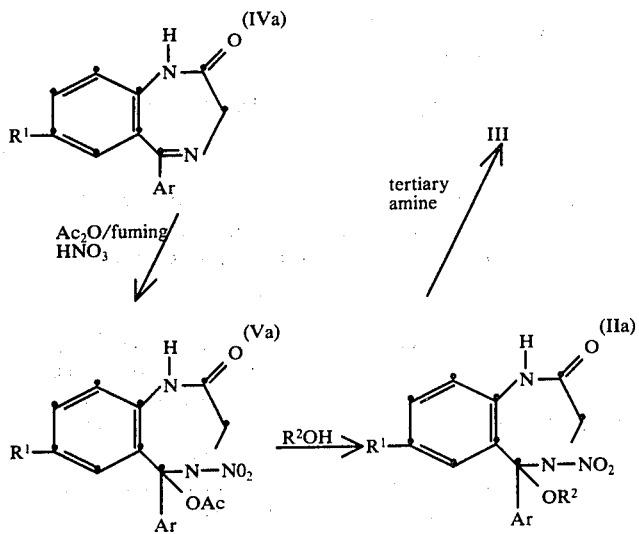

(wherein Ac, Ar, R¹, and R² each is as defined above).

Thus obtained 1,5-dihydro-2H-1,4-benzodiazepin-2-one derivatives (I) are useful as anxiolytics, sedatives, anticonvulsants, hypnotics, or their synthetic intermediates. For example, 5-methoxy-1-methyl-7-nitro-5-phenyl-1,5-dihydro-2H-1,4-benzodiazepin-2-one and 7-chloro-5-methoxy-1-methyl-5-phenyl-1,5-dihydro-2H-1,4-benzodiazepin-2-one showed $ED_{50}$ 0.69 and 0.73 mg/kg (mouse, per os.) respectively in antagonism to convulsion induced by pentylenetetrazole, while diazepam used as standard shown $ED_{50}$ 1.19 mg/kg (mouse, per os.). The other products (I) showed a similar degree of pharmacological activities. Still, the products (I) can be converted into 3-substituted-1,3-dihydro-2H-1,4-benzodiazepin-2-one derivatives by reacting with a number of nucleophilic reagents, and these are useful as their synthetic intermediates.

The 1,5-dihydro-2H-1,4-benzodiazepin-2-one derivatives (I) are applied singly or in combination with pharmaceutically suitable carriers such as wheat starch, corn starch, potato starch, gelatin, etc. The choice of carriers is determined by the preferred route of administration, the solubility of the substance, and standard pharmaceutical practice. Examples of pharmaceutical preparations are tablets, capsules, pills, suspensions, syrups, powders, and solutions. These compositions can be prepared in a conventional manner. A suitable dosage of the 1,5-dihydro-2H-1,4-benzodiazepin-2-one derivatives (I) for adults is in the order of about 1 mg to about 30 mg per day.

Presently-preferred and practical embodiments of the present invention are illustratively shown in the following examples.

EXAMPLE 1.

To a solution of sodium hydride (50% suspension in a mineral oil; 200 mg) in dry dimethylformamide (7.5 ml), 7-chloro-5-methoxy-1-methyl-4-nitro-5phenyl-1,3,4,5-tetrahydro-2H-1,4-benzodiazepin-2-one (500 mg) is added under cooling at −30° C and with stirring, and the resultant mixture is stirred at −10° C for 30 minutes. The reaction mixture is poured into icy water and shaken with diethyl ether. The organic layer is washed with water, dried over sodium sulfate, and evaporated to remove the solvent. The residue is crystallized from diethyl ether to give 7-chloro-5-methoxy-1-methyl-5-phenyl-1,5-dihydro-2H-1,4-benzodiazepin-2-one (192 mg) as colorless prisms melting at 146.5 to 147° C.

Anal. Calcd. for $C_{17}H_{15}O_2N_2Cl$: C,64.87; H, 4.80; N, 8.90; Cl, 11.26. Found: C, 64.95; H, 4.77; N, 9.06; Cl, 11.54.

Ir (Nujol): 1664, 1638, 1630 $cm^{-1}$.

EXAMPLE 2.

To a solution of 7-chloro-5-methoxy-5-phenyl-1,5-dihydro-2H-1,4-benzodiazepin-2-one (600 mg) in dry dimethylformamide (2 ml), sodium hydride (50% suspension in a mineral oil; 106 mg) is added under ice-cooling, and the resultant mixture is stirred at room temperature for 10 minutes. Methyl iodide (740 mg) is added to the mixture, which is stirred at room temperature for 5 minutes. The reaction mixture is poured into icy water and shaken with diethyl ether. The organic layer is washed with water, dried over sodium sulfate, and evaporated to removed the solvent. The residue is crystallized from isopropyl ether to give 7-chloro-5-methoxy-1-methyl-5-phenyl-1,5-dihydro-2H-1,4-benzodiazepin-2-one (381 mg) as colorless prisms melting at 146.5 to 147° C.

EXAMPLE 3.

To a mixture of 5-methoxy-7-nitro-5-phenyl-1,5-dihydro-2H-1,4-benzodiazepin-2-one (920 mg) and dry dimethylformamide (8 ml), sodium hydride (50% suspension in a mineral oil; 156 mg) is added under cooling at −30° C for 15 minutes. Methyl iodide (842 mg) is added to the mixture, which is stirred at room temperature for 10 minutes. The reaction mixture is poured into icy water, and shaken with diethyl ether. The organic layer is dried over sodium sulfate and evaporated to remove the solvent. The residue is recrystallized from methylene chloride/isopropyl ether to give 5-methoxy-1methyl-7-nitro-5-phenyl-1,5-dihydro-2H-1,4-benzodiazepin-2-one (708 mg) as fine prisms melting at 163 to 164° C.

Anal. Calcd. for $C_{17}H_{15}O_4N_3$ : C, 62.76; H, 4.65; N, 12.92. Found: C, 62.77; H, 4.74; N, 12.89.

IR (Nujol): 1667, 1640 $cm^{-1}$.

EXAMPLE 4.

A solution of 4.7-dinitro-5-methoxy-1-methyl-5-phenyl-1,3,4,5-tetrahydro-2H-1,4-benzodiazepin-2-one (400 mg) and triethylamine (1.1 g) in methylene chloride (10 ml) is allowed to stand at room temperature for 72 hours. The reaction mixture is washed with water, dried over sodium sulfate, and evaporated under reduced pressure to remove the solvent. The residue is washed with diethyl ether to give 5-methoxy-1-methyl-7-nitro-5-phenyl-1,5-dihydro-2H-1,4-benzodiazepin-2-one (196 mg) as crude product.

EXAMPLE 5.

Using 7-chloro-5-methoxy-1-methyl-4-nitro-5-(2-pyridyl)-1,3,4,5-tetrahydro-2H-1,4-benzodiazepin-2-one, the reaction if effected as in Example 1, whereby 7-chloro-5-methoxy-1-methyl-5-(2-pyridyl)-1,5-dihydro-2H-1,4-benzodiazepin-2-one is obtained.

What is claimed is:

1. A compound of the formula:

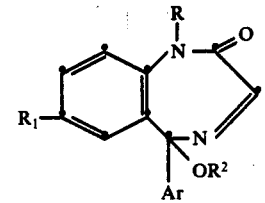

wherein Ar represents pyridyl, phenyl, or halogenophenyl; R represents $C_1 - C_6$ alkyl; $R^1$ represents halogen, nitro, trifluoromethyl, or cyano; and $R^2$ represents $C_1 - C_6$ alkyl.

2. A compound according to claim 1, wherein Ar is phenyl; R and $R^2$ is $C_1 - C_3$ alkyl; and $R^1$ is halogen.

3. A compound according to claim 2, namely 7-chloro-5-methoxy-1-methyl-5-phenyl-1,5-dihydro-2H-1,4-benzodiazepin-2-one.

4. A compound according to claim 1, wherein Ar is phenyl; R and $R^2$ each is $C_1 - C_3$ alkyl; and $R^1$ is nitro.

5. A compound according to claim 4, namely 5-methoxy -1-methyl-7-nitro-5-phenyl-1,5-dihydro-2H-1,4-benzodiazepin-2 -one.--